US010857544B2

United States Patent
Graziano et al.

(10) Patent No.: US 10,857,544 B2
(45) Date of Patent: Dec. 8, 2020

(54) DISGREGATING DEVICE OF BIOLOGICAL MATERIAL AND CORRESPONDING MANUFACTURING METHOD AND METHOD FOR THE PREPARATION OF CELL SUSPENSIONS AND TISSUE MICROGRAFTS

(71) Applicant: HUMAN BRAIN WAVE S.R.L., Turin (IT)

(72) Inventors: Antonio Graziano, Turin (IT); Riccardo D'Aquino, Turin (IT)

(73) Assignee: HUMAN BRAIN WAVE SRL, Turin (IT)

( * ) Notice: Subject to any disclaimer, the term of this patent is extended or adjusted under 35 U.S.C. 154(b) by 461 days.

(21) Appl. No.: 15/535,978

(22) PCT Filed: Dec. 14, 2015

(86) PCT No.: PCT/IB2015/059571
§ 371 (c)(1),
(2) Date: Jun. 14, 2017

(87) PCT Pub. No.: WO2016/097960
PCT Pub. Date: Jun. 23, 2016

(65) Prior Publication Data
US 2018/0236457 A1   Aug. 23, 2018

(30) Foreign Application Priority Data
Dec. 15, 2014   (IT) .............................. MI2014A2143

(51) Int. Cl.
*B02C 18/36* (2006.01)
*C12M 1/33* (2006.01)
(Continued)

(52) U.S. Cl.
CPC ............ *B02C 18/365* (2013.01); *B02C 18/10* (2013.01); *B02C 18/30* (2013.01); *B02C 18/362* (2013.01);
(Continued)

(58) Field of Classification Search
CPC ......... B02C 18/10; B02C 18/30; B02C 18/36; B02C 18/362; B02C 18/365; B02C 19/20;
(Continued)

(56) References Cited

U.S. PATENT DOCUMENTS 5,172,920 A * 12/1992 Schlenk ................. F16J 15/122
277/592
5,731,199 A * 3/1998 Roggero ................. B02C 18/10
241/194

FOREIGN PATENT DOCUMENTS

DE      3804339 A1 * 11/1988 ........... B02C 18/302
WO   02/088296 A1    11/2002
(Continued)

*Primary Examiner* — Shelley M Self
*Assistant Examiner* — Jared O Brown
(74) *Attorney, Agent, or Firm* — Arent Fox LLP; Michael Fainberg

(57) ABSTRACT

A disgregating device of biological material, comprising: a hollow outer body, defining an inner chamber; a fixed disgregating grid, having a plurality of microholes provided with sharp edges, and housed transversely in the inner chamber so as to define an upper loading chamber apt to be loaded with the biological material to be disgregated and a lower collecting chamber apt to collect the biological material, after it has been disgregated; and a bladed rotor, rotating in the inner chamber, apt to co-operate, rotating, with the fixed disgregating grid, so as to feed and bring the biological material, contained in the upper loading chamber, into contact with the microholes of the disgregating grid and
(Continued)

therefore cause the disgregation of the biological material making it pass through these microholes.

9 Claims, 13 Drawing Sheets

(51) Int. Cl.
    *B02C 19/20*     (2006.01)
    *B02C 18/30*     (2006.01)
    *C12M 3/00*     (2006.01)
    *B02C 18/10*     (2006.01)
    *G01N 1/28*     (2006.01)

(52) U.S. Cl.
    CPC .............. *B02C 19/20* (2013.01); *C12M 21/08* (2013.01); *C12M 45/02* (2013.01); *G01N 1/286* (2013.01); *G01N 2001/2866* (2013.01)

(58) Field of Classification Search
    CPC ...... C12M 21/08; C12M 45/02; C12M 47/06; G01N 1/286; G01N 2001/2866; B26F 1/14
    USPC ....... 241/84, 86, 88.1, 199.12, 2; 345/306.1; 73/864.41; 83/686
    See application file for complete search history.

(56) References Cited

FOREIGN PATENT DOCUMENTS

| WO | 2013/070899 A1 | 5/2013 |
| WO | 2014/039697 A1 | 3/2014 |

* cited by examiner

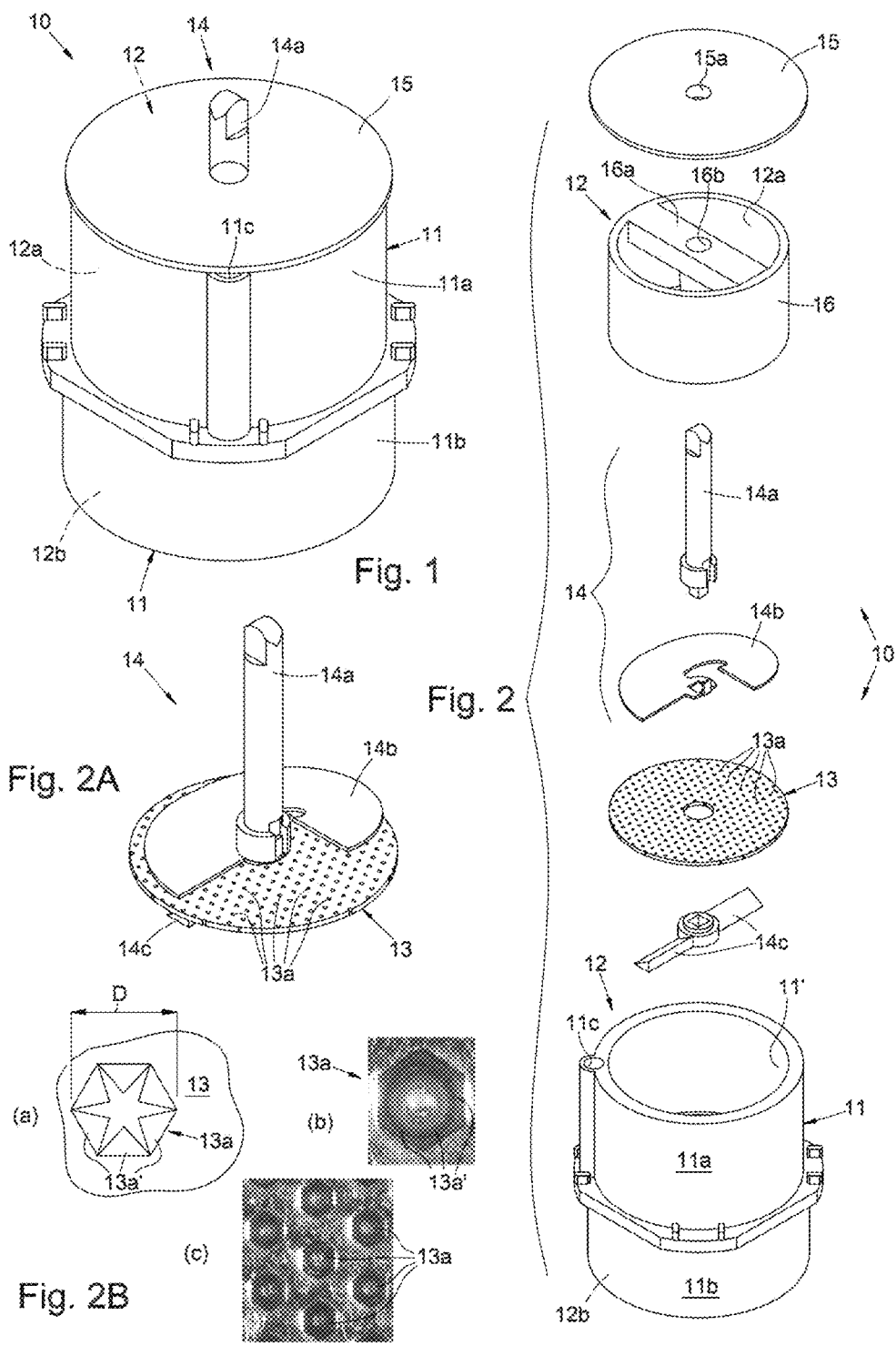

DISGREGATING DEVICE OF BIOLOGICAL MATERIAL AND CORRESPONDING MANUFACTURING METHOD AND METHOD FOR THE PREPARATION OF CELL SUSPENSIONS AND TISSUE MICROGRAFTS

This application is a National Stage entry of International Application No. PCT/IB2015/059571, filed Dec. 14, 2015, which claims priority to Italian Patent Application No. MI2014A002143, filed Dec. 15, 2014. The disclosures of these priority applications are incorporated in their entirety herein by reference.

FIELD OF THE INVENTION

The present invention relates in general to the technical sector of the systems and of the devices for disgregating and shredding biological material for various purposes and applications, and more particularly its object is a disgregating device of biological material for the preparation and setting-up of cell suspensions and tissue micrografts apt to be advantageously used for various purposes and in a plurality of applications, for example as samples for direct analyses in the laboratory, without the aid of chemical reagents, or as part of specific therapies.

The invention relates also to a corresponding method for manufacturing a disgregating device of biological material and more particularly a respective separation grid characterised by a plurality of sharp microholes through which the biological material is made to pass in order to be disgregated.

Moreover the present invention also relates to a corresponding method for preparing, by disgregation of a biological material, cell suspensions and tissue micrografts intended to be used for various purposes and in various applications, medical and otherwise, and in particular apt to be analysed, as specimens, directly in the laboratory with a microscope, without the aid of chemical reagents.

Again the invention also relates to a new cell suspension obtainable through disgregation of an original biological material, not disgregated, wherein this cell suspension is particularly advantageous and suitable for preparing samples and specimens to be analysed in the laboratory without the aid of chemical reagents.

The invention also relates to the use of a disgregating device for the preparation, by means of the disgregation of an original biological material, of cell suspensions and tissue micrografts.

Finally the invention also relates to an innovative and advantageous use wherein a disgregating device of biological material is associated with a special adapter in such a way as to be able to be advantageously connected to a surgical wand, already included in the usual supply of instruments present in the operating theatre, so as to allow the preparation, through disgregation of a biological material taken from a patient being treated in the operating theatre, of tissue micrografts to be implanted in the same patient, so that the disgregating device becomes an element and an essential part of a therapy chain, aimed at implanting tissue micrografts in a patient being treated in the operating theatre, which develops entirely inside the latter, therefore without resorting to the use of instruments and devices for the disgregation of biological material located outside the operating theatre.

BACKGROUND OF THE INVENTION AND PRIOR ART

Disgregation of a biological tissue or material, such as human, animal, vegetal tissues, is known for various purposes and as part of various applications.

For example the biological material can be disgregated in order to perform thereon medical examinations, such as a biopsy, or in general in order to obtain samples and specimens to be examined and analysed subsequently in the laboratory in order to obtain data and information, concerning the same material, to be used purely for the purpose of research or to establish a diagnosis as part of specific medical therapies.

In the prior art the biological material can also be disgregated for the purpose of isolating the cells present in the same biological material, or of setting up tissue fragments or micrografts, to be used for example in clinical and regenerative therapies, understanding a micrograft to be a set of cells, in an extracellular matrix, of subclinical size and therefore not visible to the naked eye but only with the aid of a microscope.

For completeness of information, FIG. 5 illustrates schematically a typical biological material, denoted in general by MB and for example constituted by a biological tissue, in its integral form, that is before being subjected to an operation of disgregation.

As can be seen from this FIG. 5, the biological tissue or material MB, in its intact and not yet disgregated form, typically has a plurality of cells, denoted by CEL, each one with its own nucleus NU and cytoplasm CT, which are placed in an extracellular matrix MAT, schematised with a plurality of parallel lines.

The biological material MB comprises moreover, in the respective extracellular matrix MAT, further substances and components, which are associated with the cells CEL and are for example constituted by growth factors, extracellular proteins and inorganic components, denoted by FC in FIG. 5.

In particular these growth factors and substances FC are indicative of the viability of the cells, i.e. of their ability to develop and react to the external conditions, and are also essential for allowing the cells CEL to manifest in full their properties and functions.

The prior art already offers some systems and devices which can be used by an operator to disgregate biological material in order to obtain samples of the same biological material to be used for various purposes and as part of various applications, as specified above, for example in order to perform a biopsy or an analysis of the cell compounds.

Among these known devices mention is made in particular of the triturator of biological material, described by the American patent U.S. Pat. No. 5,731,199, which comprises a cylindrical container defining an upper chamber provided to receive the biological material to be triturated; a fixed cutting member placed transversely in this chamber and constituted by a perforated plate; and a rotor, mounted rotatingly in the chamber, having a trituration element in the form of a helical blade.

The fixed perforated plate included in this mechanical triturator has a plurality of microholes, with a preferably square or hexagonal profile, having a diameter or a size which is comprised between 20 and 100 µm, wherein the edges of each microhole define trituration blades.

In the use of this triturator the trituration element, rotating, co-operates with the cutting member, i.e. the perforated plate, so as to feed and bring the biological material, contained in the upper chamber, into contact with the blades of the microholes of the cutting member and therefore cause the trituration of the biological material making it pass through these microholes.

This triturator device is not however free from limits and disadvantages, which it would be appropriate to remedy, in particular in order to make the samples which are obtained from the disgregation of the original biological material suitable to be advantageously used in a wider number of applications and situations, with respect to what is now possible, both in the field of laboratory analyses and of therapies.

In fact, as it was possible to note experimentally, the mechanical disgregator known from this patent U.S. Pat. No. 5,731,199, as also other similar devices, produces a sample of disgregated biological material in which the cell or cells are separated from their biological niche or "habitat", so that the cell or cells present in the biological sample, produced in this way, can have a form, functions and a viability which have in some way been modified and altered with respect to the original biological material.

For clarity, FIG. 6 shows schematically a cell obtained by disgregating the original biological material with a conventional disgregating device, in other words in accordance with the prior art.

As can be seen from this FIG. 6, the cell or cells present in the material disgregated with a disgregating device of conventional type, as well as being separated and no longer associated with their biological niche which surrounded them in the original biological material, have a substantially modified form with respect to the initial one.

As a result, in the prior art, for the very reason that it may occur and in any case there is a real risk that the sample is altered in some way and undergoes changes during the phase of disgregation with respect to the original biological material, often use is made of chemical reagents or in general further substances for preparing, from the triturated biological material, the specimens and samples to be analysed, or to set up the cell suspensions and micrografts foreseen by the various clinical therapies and treatments.

Moreover, given that the structure, the functions and the viability of the cells could have been modified and altered during the phase of disgregation performed with conventional techniques, there is always the uncertainty that the data and the information obtained from the analyses of the samples, obtained in this way, are not exactly corresponding to and indicative of the original and not yet disgregated biological material.

SUMMARY OF THE INVENTION

Therefore a first object of the present invention is to propose and make a new disgregating device of biological material which offers improved performances compared to known disgregators and in particular allows the obtaining of biological samples, achieved through disgregation of an original biological material, in which the cells maintain their form and their niche and biological habitat and therefore their functional viability with which they were associated in the original biological material, so as to allow the obtaining of more accurate data from the analyses of the samples obtained, as also an improved and more advantageous application of these samples as part of laboratory analysis and diagnosis and medical therapy.

A second object of the present invention, moreover related to the first, is also that of proposing and making a new disgregating device of biological material which is a significant innovation with respect to the mechanical triturator known from the U.S. Pat. No. 5,731,199, cited previously, and in particular, for this purpose, comprises a fixed perforated plate with a plurality of microholes, for the disgregation of biological material, which have an optimised configuration and moreover are made via an innovative manufacturing process, so as to involve performances considerably higher than those which can be obtained with the mechanical triturator proposed by the U.S. Pat. No. 5,731,199 and in particular allow tissue micrografts to be set up and cell suspensions to be prepared, characterised by a high viability of the respective cells, which can be used in various medical and non-medical applications.

A third object of the present invention, again related to the previous ones, is also that of proposing and making a new disgregating device of biological material which allows the setting-up of tissue micrografts and the preparation of cell suspensions, usable for various purposes for example for laboratory tests and clinical therapies, without the aid of and having to use chemical reagents for the making of the same tissue micrografts and cell suspensions.

A further object of the present invention is also that of proposing a method for obtaining, through disgregation of an original biological material, samples and specimens of biological material, such as tissue grafts and cell suspensions, which can be advantageously used in a vast range of applications and circumstances in the field of research, laboratory analyses and medical therapy.

The abovementioned objects can be considered achieved in full by the disgregating device of biological material for the preparation of cell suspensions and tissue micrografts, having the features defined by the independent claims of the present disclosure, by the disclosed method for the manufacturing of a disgregating device of biological material, and by the disclosed method for preparing, through disgregation of an original biological material, cell suspensions and tissue micrografts.

Particular embodiments of the present invention are moreover defined by the dependent claims.

There are numerous advantages, in part already implicitly disclosed previously, with respect to the disgregating devices and systems currently known and in use, which are associated with the disgregating device of biological material, for the preparation and setting-up of cell suspensions and tissue micrografts, in accordance with the present invention, as listed here below, purely by way of an example:

capacity of the device for preparing micrografts and cell suspensions which maintain intact and unaltered the features of the initial original biological material, not yet disgregated, and therefore avoid the use of chemical reagents for preparing these tissue micrografts and cell suspensions;

use of the tissue micrografts and of the cell suspensions prepared with the disgregating device in new and innovative medical, veterinary and cosmetic treatments;

possibility of performing more accurate and reliable analyses using as specimens and samples to be analysed the tissue micrografts and the cell suspensions prepared with the disgregating device.

possibility of inserting the disgregating device in a therapy chain, involving the use of disgregated biological material to be inserted and implanted in a patient being treated in the operating theatre, wherein the therapy chain is performed completely inside the same operating theatre, that is to say without the need to have to transfer outside the latter the biological material, to be disgregated, taken from the patient being treated in the operating theatre.

BRIEF DESCRIPTION OF THE DRAWINGS

These and other objects, features and advantages of the present invention will be made clearer and evident by the following description of one of its preferred embodiments, given by way of a non-limiting example, with reference to the accompanying drawings, in which:

FIG. 1 is an axonometric view of a disgregating device of biological material for the preparation of cell suspensions and the setting-up of tissue micrografts in accordance with the present invention;

FIG. 2 is an axonometric view, in exploded form, which shows the parts of the disgregating device of biological material of FIG. 1;

FIG. 2A is a perspective view, on an enlarged scale, of a bladed rotor and of a disgregating grid of the disgregating device of FIGS. 1 and 2:

FIG. 2B, divided into sections (a), (b) and (c), is a view which shows in plan and on an enlarged scale, with the aid of some photographic images, a single microhole and a group of microholes of the disgregating grid of FIG. 2A.

DESCRIPTION OF SOME PREFERRED EMBODIMENTS OF THE DISGREGATING DEVICE OF BIOLOGICAL MATERIAL ACCORDING TO THE INVENTION

Figure 5:
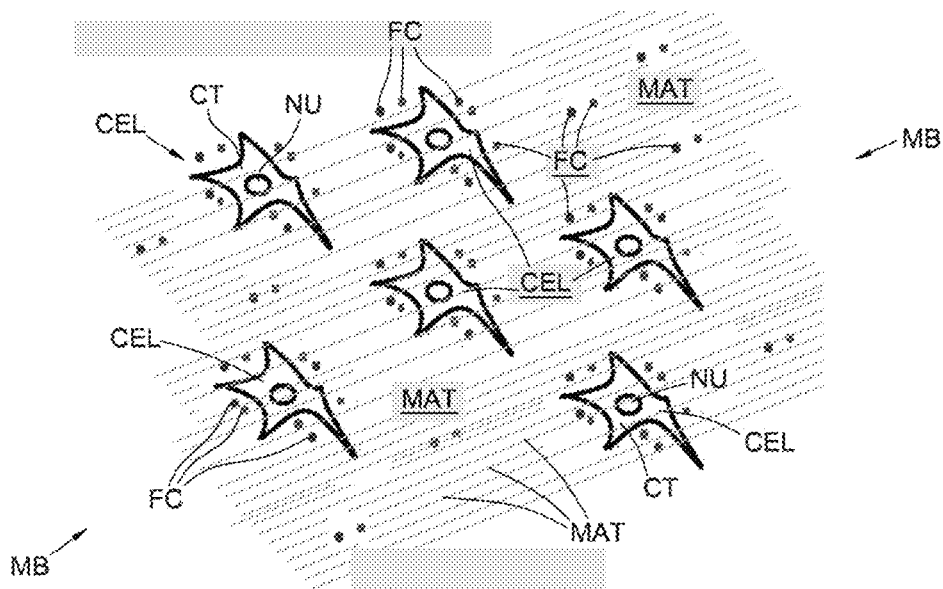
FIG. 5 is a diagram which illustrates the typical structure of a biological tissue before being disgregated.

Referring to the drawings and in particular to FIGS. 1-3 a disgregating device of biological material MB, such as for example the biological tissue illustrated schematically in FIG. 5, made in accordance with the present invention, is denoted overall by 10.

As further explained here below, the disgregating device 10 is particularly suitable and advantageous for preparing cell suspensions and setting up tissue micrografts, understanding a tissue micrograft, in line with what has already been explained previously, to be a cell suspension or a set of cells, in an extracellular matrix, of subclinical size and therefore not visible to the naked eye but only with the aid of a microscope.

In detail the disgregating device 10 of biological material MB is composed of the following parts:

a hollow outer body, denoted by 11, with a substantially cylindrical shape, defining an inner chamber 12;

a fixed disgregating grid or plate 13, having a plurality of microholes 13a each one provided with sharp edges, which is housed transversely in the inner chamber 12 defined by the outer body 11, so as to define in turn an upper loading and receiving chamber, denoted by 12a, apt to receive and be loaded with the biological material to be disgregated MB, and a lower collecting chamber, denoted by 12b, apt to collect the biological material, once disgregated, denoted by MB';

a bladed rotor 14, rotating in the inner chamber 12 and apt to co-operate, rotating, with the fixed disgregating grid 13, so as to feed and bring the biological material MB, contained in the upper loading chamber 12a, into contact with the microholes 13a, with sharp edges, formed in the disgregating grid 13, and therefore cause the disgregation of the biological material MB making it pass through these microholes 13a; and a cover 15 for covering the upper loading chamber 12a.

The bladed rotor 14, rotating, included in the disgregating device 10, in turn is constituted by:

a shaft 14a, oriented in vertical direction, having an upper portion which extends in a hole 15a formed in the cover 15 and projects above from the latter;

a distributing blade or vane 14b, associated with a lower end of the vertical shaft 14a and exhibiting a curved helical shape; and a lower scraper 14c, also associated with the lower end of the vertical shaft 14a, wherein the fixed perforated disgregating grid 13 is interposed between the helical blade 14b and the lower scraper 14c associated with the lower end of the shaft 14a, whereby the bladed rotor 14 is suitable to co-operate, rotating, through its helical blade 14b and its lower scraper 14c, respectively with an upper face, of the disgregating grid 13, turned towards the upper loading chamber 12a, in order to bring the biological material MB to be disgregated into contact with the microholes 13a of the disgregating grid 13, and with a lower face, of the disgregating grid 13, turned towards the lower collecting chamber 12b, in order to scrape the disgregated biological material MB' that comes out from the microholes 13a of the disgregating grid 13 and discharge it in the lower collecting chamber 12b as described further here below.

The cylindrical outer body 11, included in the disgregating device 10 of the invention, is in turn associated with a secondary internal body 16, defining the upper loading chamber 12a, and is constituted by an upper portion 11a which defines a seat 11' which houses this secondary inner body 16 and a lower portion 11b that defines the lower collecting chamber 12b, wherein the perforated disgregating grid 13 is interposed between this secondary inner body 16, housed in the respective seat 11' defined by the upper portion 11a of the outer body 11, and the lower portion 11b, defining the lower collecting chamber 12b, of the outer body 11.

Moreover the outer body 11 of the disgregating device 10 defines a through hole 11c which extends in vertical direction in the external cylindrical wall of the same outer body 11, between an upper edge of the upper portion 11a and the base of the lower collecting chamber 12b, corresponding to the lower portion 11b, so as to traverse these two portions 11a and 11b of the outer body 11.

Therefore this vertical through hole 11c is suitable for placing in communication the exterior of the disgregating device 10 with the lower collecting chamber 12b, in order to allow the extraction from the same lower collecting chamber 12b of the disgregated biological material MB', as described in greater detail here below.

The secondary internal body 16, associated with the outer body 11, in turn has a portion 16a defining a hole 16b which houses rotatably the shaft 14 of the bladed rotor 14, and is moreover attached to the upper portion 11a of the outer body 11 so as not to rotate and thus avoid any rotation of the perforated disgregating grid 13, interposed between the same secondary internal body 16 and the lower portion 11b, defining the lower collecting chamber 12b, of the outer body 11, when the bladed rotor 14 rotates in the inner chamber 12 to cause the disgregation of the biological material MB, as illustrated more clearly here below when describing the working of the disgregating device 10.

The outer body 11, the cover 15, the secondary internal body 16 and the shaft 14a of the bladed rotor 14 are in biocompatible plastic material, while the perforated disgregating grid 13 and the distributing blade 14b of the bladed rotor 14 are in stainless steel, of the type suitable for the manufacture of instruments for surgical uses.

As can be seen from the drawings all the various component parts of the disgregating device 10 are assembled by pressure without the aid of bonding agents and/or tools, and can therefore be dismantled.

Given the great importance, in the sphere of the present invention, as will be made clear further on in the description, of the microholes 13a, which characterise and are formed in the disgregating grid 13, in particular in relation to their specific dimensions and configuration, these microholes 13a will now be described in a detailed manner, also as regards the respective manufacturing process.

The Microholes of the Disgregating Grid of the Disgregating Device of the Invention and the Relative Manufacturing Process According to a feature of the present invention the microholes 13a of the perforated disgregating grid or plate 13 have size or a diameter, denoted by D in FIG. 2B, which is comprised between 70 and 80 μm, and more preferably have a size or diameter D of about 75 μm.

Thanks to this feature, as has emerged from thorough tests and experiments, it is possible by means of the device 10 of the invention to set up tissue micrografts and prepare cell suspensions, usable for various purposes and applications, for example as specimens and samples simply to be analysed for research purposes or usable in the diagnosis and therapy of certain pathologies, which maintain integral and unaltered the features, functions and cell viability of the original biological material MB, in this way avoiding the use of chemical reagents for preparing these tissue micrografts and cell suspensions, as instead is often necessary in the prior art.

According to a further feature of the present invention, also apt to allow the considerable and advantageous performances of the disgregating device 10 of the invention, as illustrated above, the microholes 13a of the disgregating grid or plate 13 are formed by means of a special moulding and forming process, by means of a mould S of the die-punch type, of a sheet or a leaf or a metal strip, in particular made up of a strip of AISI 316L stainless steel.

Figure 2C:
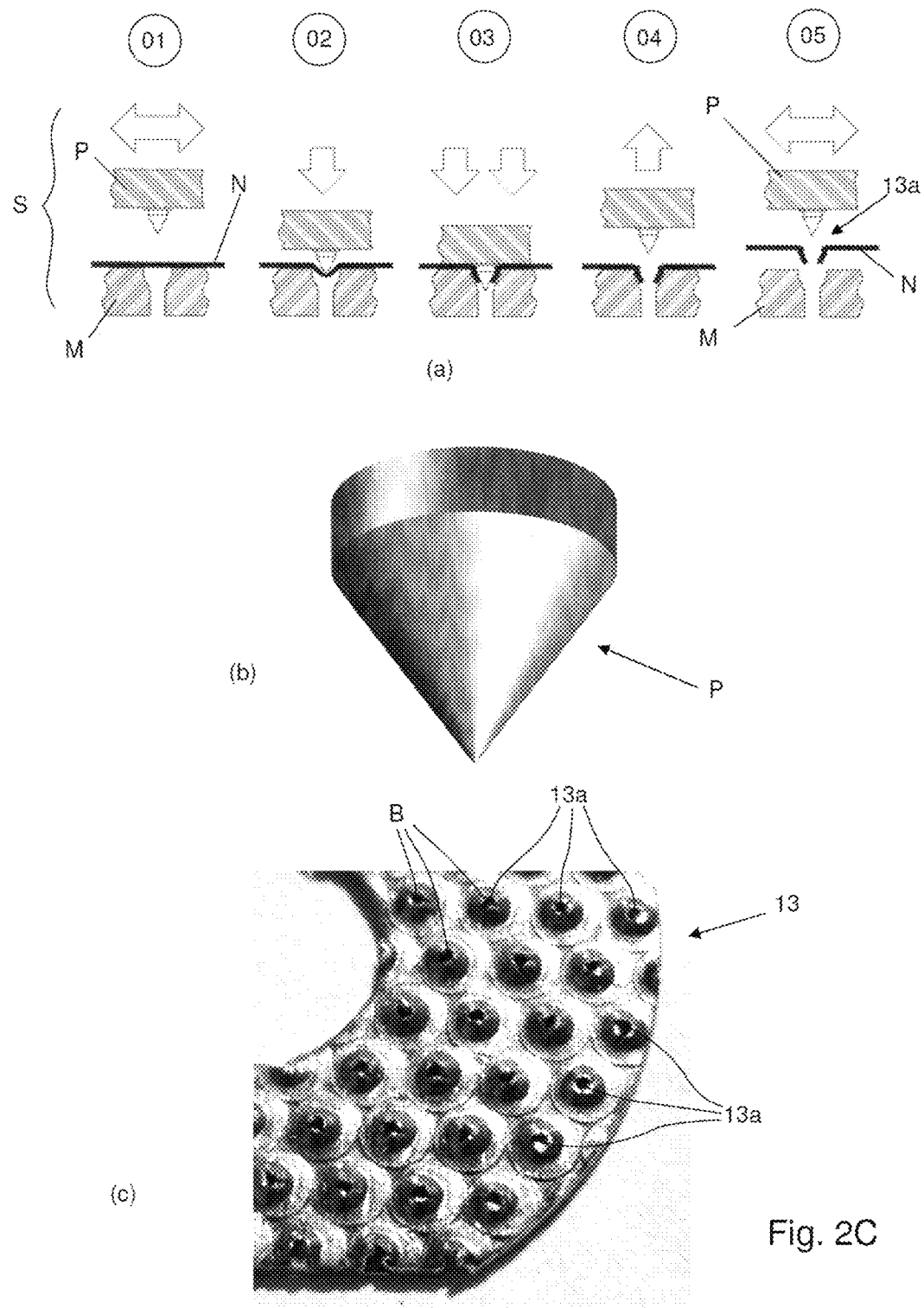
FIG. 2C, divided into sections (a), (b) and (c), shows respectively, in the section (a), a diagram aimed at illustrating the various phases of a first embodiment of a manufacturing process, by moulding, of the microholes of the disgregating grid included in the disgregating device of biological material of the invention; in section (b) a conical punch used in the manufacturing process, by moulding, schematised in section (a); and, in section (c), a photographic image of the disgregating grid obtained with this manufacturing process, by moulding.

FIG. 2C shows schematically, in the respective section (a), the various steps of a first embodiment of this process of manufacturing and forming by moulding of the microholes 13a of the disgregating grid 13 included in the disgregating device 10 of biological material of the invention.

In detail the process of manufacturing by moulding of the microholes 13a, in accordance with this first embodiment, comprises the following steps 01-05 illustrated in FIG. 2C-section (a) with the aid of arrows:

01 positioning of the strip or leaf N of AISI 316L stainless steel between the punch, denoted by P, and the die, denoted by M, of the mould S;

02 descent of the punch P from an upper dead point and consequent forming of the strip or leaf N of AISI 316L stainless steel;

03 stop of the punch P, at the end of its descent stroke, against the die M, with final forming and consequent fracturing of the material of the metal leaf N at the centre of the punch P;

04 return of the punch P to the respective upper dead point;

05 extraction, from the die M, of the leaf N formed and perforated.

The punch P used in this first embodiment of the process of manufacturing and forming of the microholes 13a has a conical and pointed configuration, as clearly shown in FIG. 2C-section (b).

Moreover, for completeness of information, FIG. 2C-section (c) shows a photographic image of a portion of the disgregating grid 13, obtained with the process of manufacturing by moulding schematised in section (a) of the same FIG. 2C, wherein this photographic image clearly highlights the configuration of the microholes 13a and in particular how each of them has an orifice with sharp edge B, as the effect of the tearing or of the breakage, caused by the process of manufacturing by moulding, of the material of the original strip N.

More particularly it is pointed out that the orifice that is created through tearing, or breakage of the material of the strip N, at the top of the respective drawn area, by the action of the conical punch P in co-operation with the die M, is not regular but has a sharp jagged edge, through the effect of the breakage of the material of the strip N.

In practice, by dimensioning in an appropriate manner the die M and the punch P it is possible, in this first embodiment illustrated in FIG. 2C of the process for manufacturing the grid 13, to obtain the orifices of the microholes 13a through the effect of the breakage of the material constituting the strip N, wherein the orifice of each microhole 13a has an irregular shape and edge, sharp, as shown in the photographic image of FIG. 2C-section (c).

The average size or the average diameter of the microholes 13a generated in this way by the breakage of the material of the strip N can vary from a minimum of 50 microns to a maximum of 200 microns.

Figure 2D:
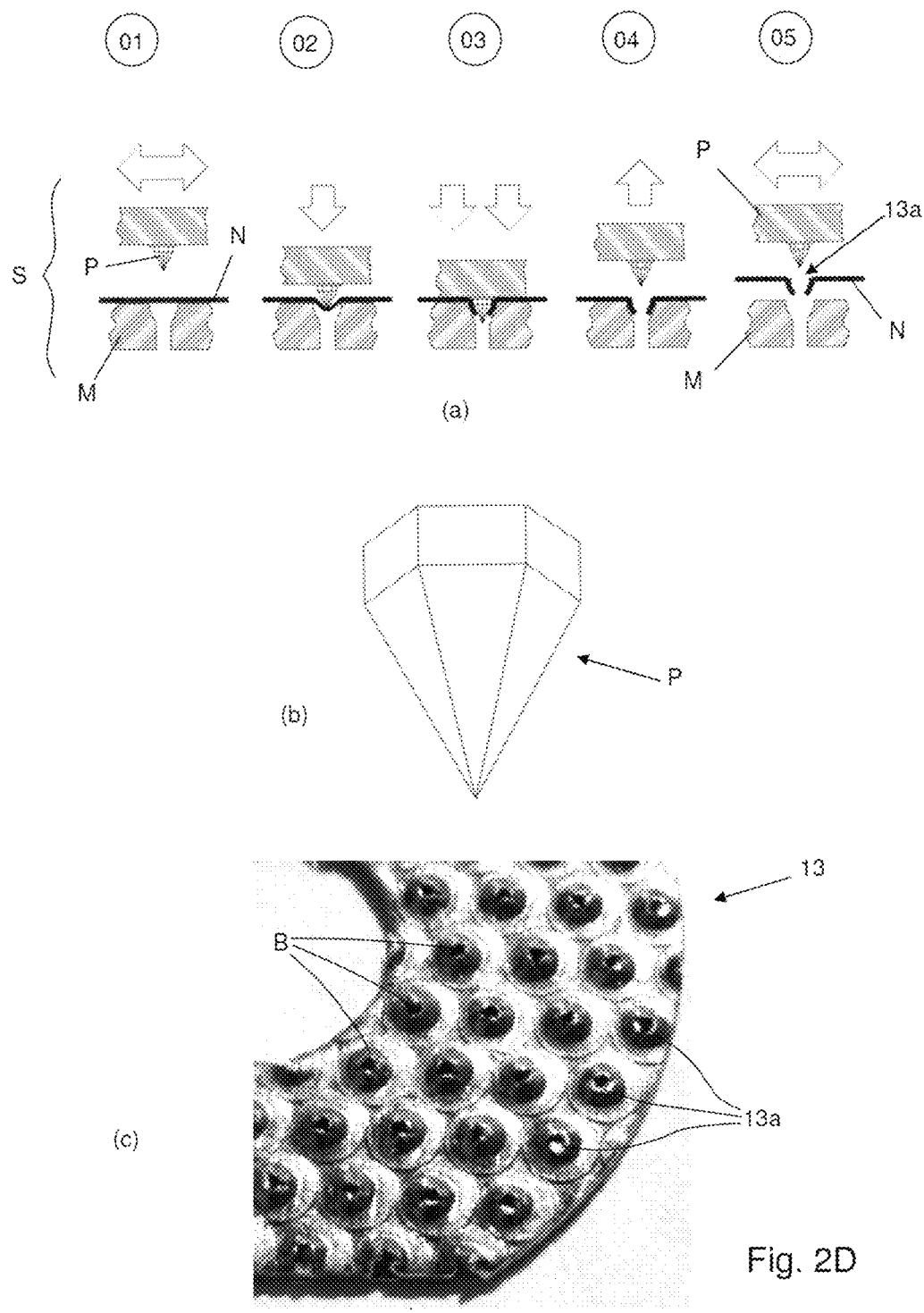
FIG. 2D, divided into sections (a), (b) and (c), shows respectively, in the section (a), a diagram aimed at illustrating the various phases of a second embodiment of the manufacturing process, by moulding, of the microholes of the disgregating grid included in the disgregating device of biological material of the invention; in section (b) a polygonal punch used in the manufacturing process, by moulding, schematised in section (a); and, in section (c), a photographic image of the disgregating grid obtained with this manufacturing process, by moulding.

FIG. 2D in turn shows schematically, in the respective section (a), the various steps of a second embodiment of the process of manufacturing and forming by moulding of the microholes 13a of the disgregating grid 13 included in the disgregating device 10 of biological material of the invention.

The process of manufacturing by moulding of the microholes 13a, in accordance with this second embodiment, differs from that of the first embodiment, described previously with reference to FIG. 2C, in that the punch P has a polygonal configuration, as clearly shown in FIG. 2D-section (b), instead of conical.

In detail the process of manufacturing by moulding of the microholes 13a, in accordance with this second embodiment, comprises the following steps 01-05 illustrated in FIG. 2D-section (a) with the aid of arrows:

01 positioning of the strip or sheet or leaf N of AISI 316L stainless steel between the punch, denoted by P, and the die, denoted by M, of the mould S;

02 initial descent of the punch P from an upper dead point with consequent deformation and forming of the material of the strip or sheet N of AISI 316L stainless steel;

03 stop of the punch P, at the end of its descent stroke, against the die M, with final forming and fracturing of the material of the sheet N at the centre of the punch P;

04 return of the punch P to the upper dead point;

05 extraction, from the die M, of the sheet N formed and perforated.

Moreover, for completeness of information, FIG. 2D-section (c) shows a photographic image of a portion of the disgregating grid 13, obtained with the process of manufacturing by moulding schematised in section (a) of the same FIG. 2D and in accordance with the second embodiment, wherein this photographic image clearly highlights the configuration of the microholes 13a and in particular how the orifice, defined by each of them, has a sharp edge B, as the effect of the tearing or of the breakage, caused by the process of manufacturing by moulding, of the material of the original strip N.

In practice, by dimensioning in an appropriate manner the die M and the punch P it is possible, in this second embodiment illustrated in FIG. 2C of the process for manufacturing the grid 13 and similarly to the first embodiment illustrated in FIG. 2C, to obtain the orifices of the microholes 13a through the effect of the breakage of the material constituting the sheet N, wherein the orifice of each microhole 13a has an irregular shape and edge, sharp, as shown in the photographic image of FIG. 2D-section (c).

Moreover it is pointed out that the use of the punch P, with polygonal configuration, in this second embodiment of the process of manufacturing of the microholes 13a, allows advantageously the formation of microholes 13a, each one exhibiting a sharp edge characterised by several sharp tips, in turn corresponding in number to that of the sides of the polygonal configuration of the punch P.

In this respect it is also pointed out, as ascertained by numerous and thorough experimental tests, that excellent results were obtained with a disgregating device 10 having a disgregating grid 13 characterised by microholes 13a each one exhibiting a hexagonal configuration, with six sharp tips, in turn obtained using a hexagonal punch in this process of moulding illustrated in FIG. 2D.

To sum up the microholes 13a of the disgregating grid 13, constituting, together with the distributing blade 14b, the working structure of the disgregating device 10, are obtained with a process of moulding of the punch-die type which causes the breakage of the material of a sheet of stainless steel, so that through the effect of this breakage each microhole 13a has a respective irregular edge having sharp features, in particular defining a plurality of microblades.

For example, advantageously, as already specified previously, the microholes 13a can have a hexagonal shape as shown in FIG. 2B, in particular obtained using a hexagonal punch in the process of manufacturing illustrated in FIG. 2D.

Naturally other shapes and configurations are possible, for example round or square, etc., or in general polygonal, wherein the microblades of each microhole 13a correspond to the sides of the respective polygon.

In particular, for greater clarity, FIG. 2B shows in detail, with the aid of some photographic images obtained from a prototype of the disgregating device 10 of the invention, both a single hole 13a and a group of holes 13a which are formed in the disgregating grid 13, wherein the microblades which are associated with the sides of each hexagonal hole 13a are denoted by 13a'.

Figure 2E:
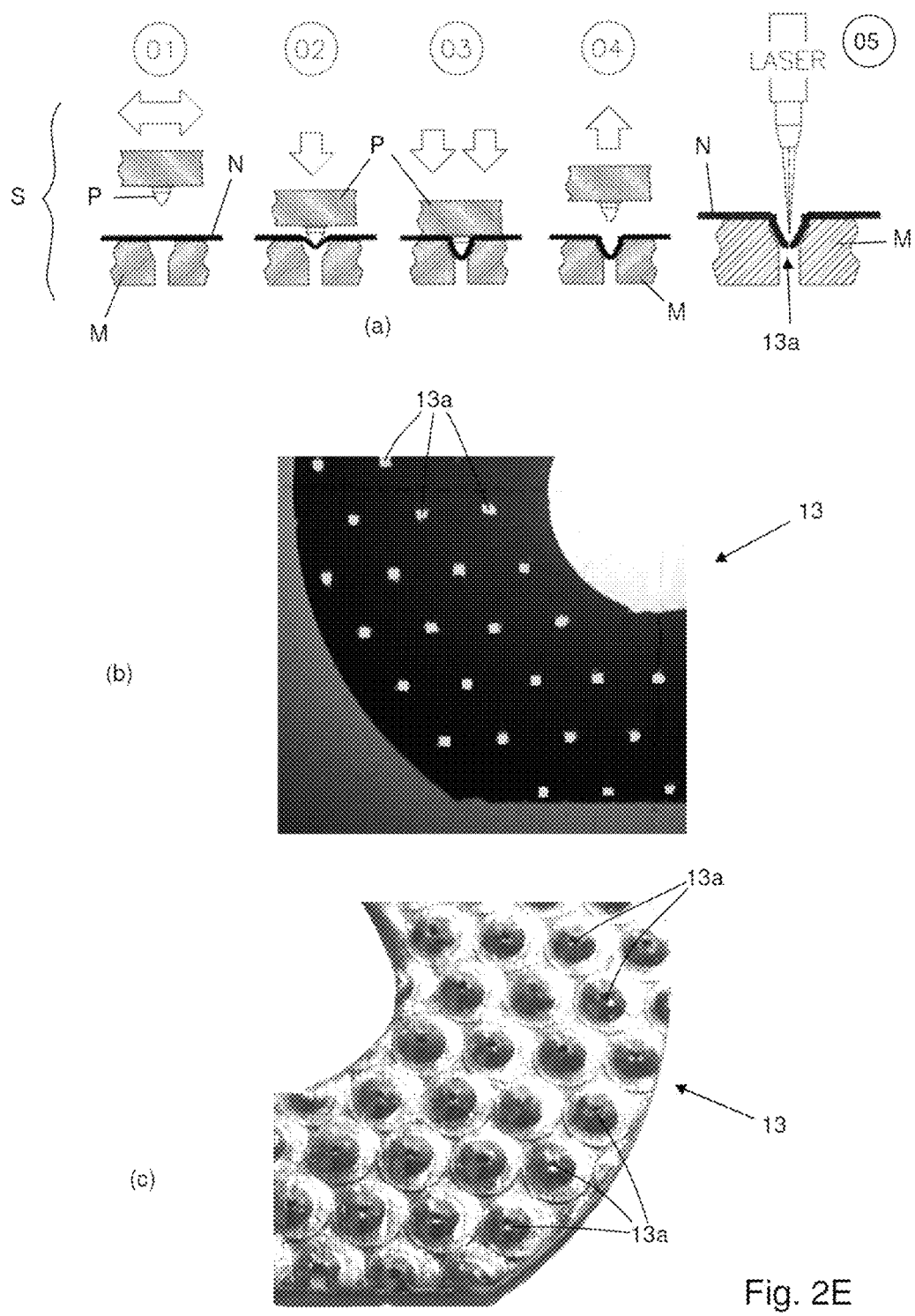
FIG. 2E, divided into sections (a), (b) and (c), shows respectively, in the section (a), a diagram aimed at illustrating the various phases of a third embodiment, including a phase of drilling by means of a laser source, of the manufacturing process, by moulding, of the microholes of the disgregating grid of the disgregating device of biological material of the invention; and in sections (b) and (c) a first and second photographic image which show the disgregating grid and the respective microholes, made by means of the laser source, obtained by the manufacturing process, schematised in section (a), in accordance with this third embodiment.

Finally FIG. 2E shows schematically, in the respective section (a), the various phases of a third embodiment of the process of manufacturing and forming by moulding of the microholes 13a of the disgregating grid 13 included in the disgregating device 10 of biological material of the invention.

The process of manufacturing by moulding of the microholes 13a, in accordance with this third embodiment, differs from those of the first and of the second embodiments, described previously with reference to FIGS. 2C and 2D, in that the punch P, used in the process, has at the tip a rounded and not pointed configuration, so that the punch P is configured so as to deform and draw only the material of the strip N, but without causing the tearing and the fracture thereof, and moreover in that the orifice of the final microhole 13a is obtained, instead of by tearing and fracture of the material of the strip N, by means of a laser (light amplification by stimulated emission of radiation) source.

In detail the process of manufacturing of the microholes 13a, in accordance with this third embodiment, comprises the following steps 01-05 illustrated in FIG. 2E-section (a) with the aid of arrows:

01 positioning of the strip or sheet N of AISI 316L stainless steel between the punch P and the die M, of the mould S;

02 initial phase of the descent of the punch P from an upper dead point and consequent forming of the material of the strip or sheet N of AISI 316L stainless steel;

03 stop of the punch P, at the end of its descent stroke, against the die M, with forming and drawing of the strip N, without however causing the tearing and the fracture of the material constituting this strip N;

04 return of the punch M to the upper dead point and its removal from the zone of the strip N;

05 performance of the drilling, or perforation of the material of the strip N which forms the tip of the drawn zone, by means of a laser source, in particular of the type having a multifocal head;

For completeness of information, FIG. 2E-sections (b) and (c) shows two photographic images of a portion of the disgregating grid 13 which is obtained with the process of manufacturing, schematised in section (a) of the same FIG. 2E, in accordance with this third embodiment and using a source of laser light, wherein these photographic images highlight and show in detail the apertures or the orifices formed by means of the source of laser light.

It is pointed out that the orifice which is created and obtained in this way with the laser, in the interior and in the central region of the zone drawn by means of the punch P, is particularly precise, and that this laser technique allows the orifice to be made with dimensions as required, in the particular in the range of 50-70 μm (microns) with a tolerance of ±5 μm (microns).

Moreover the cut, made in this way by the laser, in turn appropriately calibrated for the type of cut required in order to form the orifice, has particularly sharp edges.

Again with the laser particularly complex cut figures can be obtained, such as for example a rhomboid cut, such as that preferably used, oval, cross, or a simple round hole.

Working of the Disgregating Device 10 of the Invention

As specified previously the disgregating device 10 of the invention was specifically designed to shred and disgregate finely a biological material in order to obtain therefrom a cell suspension or a tissue micrograft and can be operated in the following way.

Initially, after having opened and extracted completely the cover 15 from the cylindrical outer body 11, a pre-established quantity of a physiological solution is introduced into the upper loading chamber 12a which will therefore accumulate on the base of this loading chamber 12a.

This physiological solution has the function of performing an action of lubrication during the entire process of disgregation of the biological material and, also and above all, that of operating as a means of recovering the disgregated biological material obtained at the end of the disgregation process.

Then the sample, i.e. the biological material MB to be disgregated, is loaded into the upper loading chamber 12a, in turn in such dimensions as to allow the distributing blade 14b to surmount this biological material MB in the initial phase of the disgregation process.

Then, after having closed again the disgregating device 10 with the upper cover 15, it is ensured that the disgregating device 10 is in a vertical and stable position so that it cannot rotate during the subsequent phase of disgregation.

At this point the part, projecting from the cover 15, of the shaft 14a of the bladed rotor 14 is coupled with appropriate motor means, for example constituted by an electric motor, provided to drive the rotation of the bladed rotor 14.

In particular, in this phase, it can be useful and advantageous to use an appropriate adapter, described here below in a more accurate and detailed manner, to couple the projecting part of the shaft 14a with the electric motor.

Subsequently the motor is actuated so as to drive the rotation of the rotor 14, as indicated by arrows f1 in FIG. 3B, for a prefixed time, i.e. until the conclusion of the disgregation cycle.

In detail, during this disgregation phase, the distributing blade 14b of the bladed rotor 14, rotating, distributes and brings the biological material MB loaded in the upper loading chamber 12a into contact with the microholes 13a formed in the disgregating grid 13, forcing it to pass through them, so that the biological material MB, passing through these microholes 13a and co-operating with the respective microblades, is appropriately disgregated.

Figure 3A:
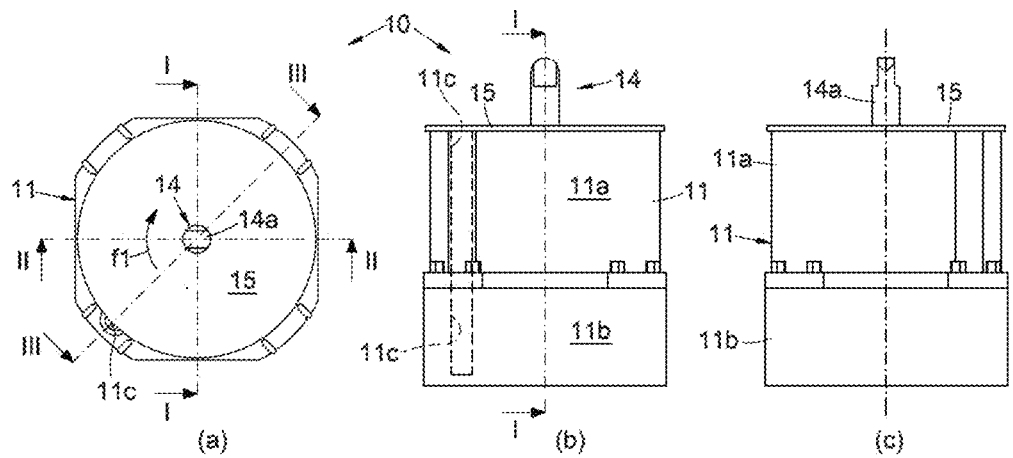
FIG. 3A, divided into sections (a), (b), (c), is an orthogonal view which shows in a plan view and laterally the disgregating device of biological material of FIGS. 1 and 2.
Figure 3B:
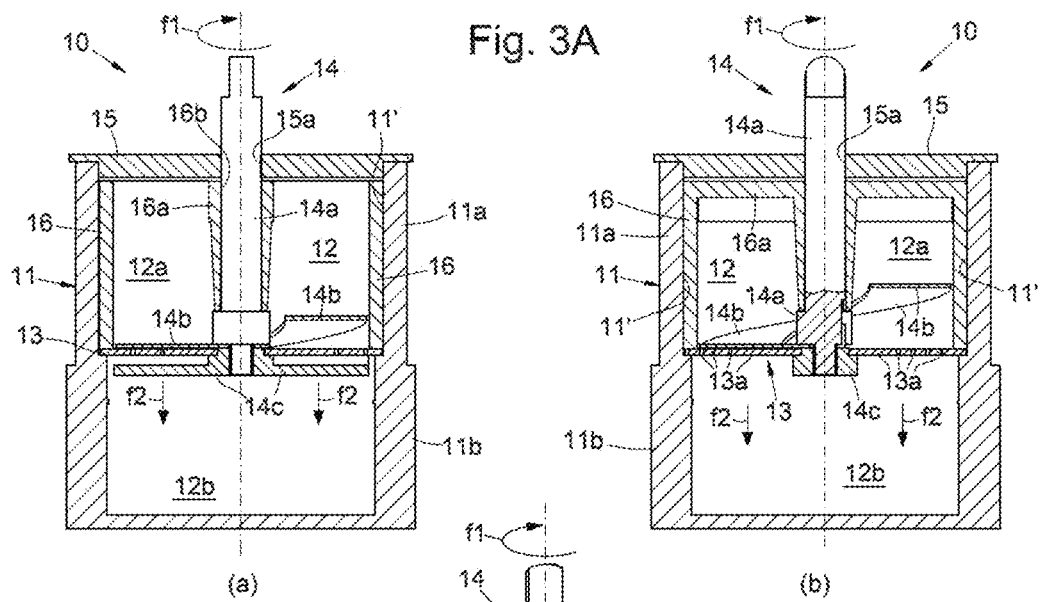
FIG. 3B, divided into sections (a), (b), (c), shows on an enlarged scale and sectioned, respectively along lines I-I, II-II and III-III of section (a) of FIG. 3A, the disgregating device of biological material of the invention.

Moreover the scraper 14c, rotating integrally with the distributing blade 14b, encourages the detachment of the disgregated biological material MB', after it has passed through the microholes 13a, from the lower surface of the disgregating grid 13, and its collection on the base of the collecting chamber 12b, as schematised with dotted and dashed line and indicated by arrows f2 in FIG. 3B.

In this phase, purely by way of an example and therefore without wanting to restrict in any way the range of use and application of the disgregating device 10 of the invention, the bladed rotor 14 can be made to rotate at a speed of approximately 80 rpm, applying moreover thereon an appropriate torque, for example of 25 Nw*cm, in order to overcome the usual mechanical resistances which oppose this rotation, and therefore cause the passage of the biological material through the grid 14 and its consequent disaggregation.

Finally, at the end of the disgregation phase, after having disconnected the electric motor from the shaft 14a of the bladed rotor 14, a syringe is inserted, of the type without needle, inside the hole 11c which extends vertically in the wall of the cylindrical outer body 11, and the cell suspension or the disgregated biological material MB', obtained in this way, is aspirated from the lower collecting chamber 12b, as indicated schematically by arrows f3 in FIG. 3B.

Technique of Shredding/Disgregating the Biological Material at the Base of the Device of the Invention It is therefore clear from what has been described hitherto, with regard both to the structure and to the working of the disgregating device 10, that the present invention implies also a new and innovative technique of shredding/disgregating of a biological material MB.

In particular, on the basis of this innovative technique, due to the rotation of the bladed rotor 14 the biological material MB is initially driven and brought into contact with the disgregating grid 13 by the distributing blade 14b which surmounts the biological material MB inside the loading chamber 12a.

Therefore in this initial phase the physiological solution, already contained in the loading chamber 12a, is enriched with cells.

Moreover the bladed rotor 14, while it rotates, performs the dual function of rotating the biological material and of moving the physiological solution so as to mix them.

Again the distributing blade 14b of the bladed rotor 14, being appropriately shaped along a helical profile, ensures that, during the phase of disgregation of the biological material MB, the physiological solution, contained in the loading chamber 12a, washes continuously the surface of the disgregating grid 13.

This continuous distribution of the physiological solution in contact with the perforated disgregating grid 13 in turn is such as to continuously clean the respective holes 13a and therefore allow the free passage through them of the cells, so as to avoid overheating and/or burning of the tissues and of the cells or other disadvantages which could alter the features of the original biological material MB, during the sliding of the distributing blade 14b on the disgregating grid 13.

Finally the sliding and the light pressure exerted by the distributing blade 14b, while it rotates, on the biological material MB to be shredded, mean that the cells or the agglomerates of cells, having a maximum diameter smaller than 75 microns, are forced to pass through the holes 13a, appropriately calibrated, of the disgregating grid 13, so that from the opposite side of the perforated grid 13 only the cells or the agglomerates of cells, included in the biological material MB, come out which have a maximum diameter smaller than 75 microns.

In particular it is underlined and confirmed again that this exact and precise size of 75 μm of the through holes 13a formed in the disgregating grid 13 is of fundamental importance for obtaining, at the end of the disgregation process, a cell suspension which has conserved intact the features, functions and viability of the original biological material, not disgregated.

Figure 5A:
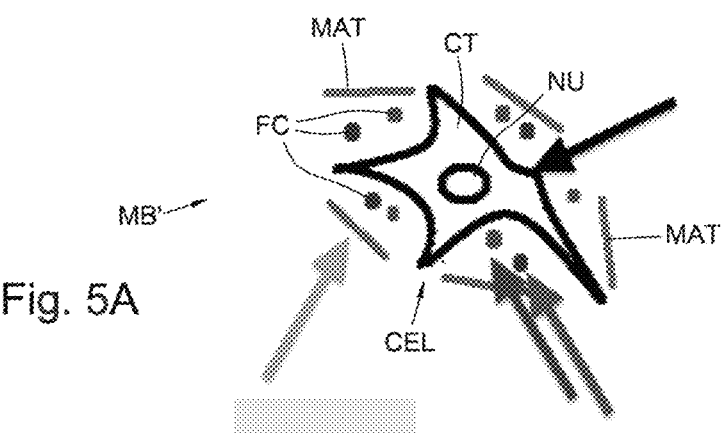
FIG. 5A is a diagram which illustrates a cell suspension obtained with the disgregating device of the invention of FIGS. 1 and 2.

For greater clarity, FIG. 5A shows schematically a cell suspension obtained through disgregation of an original biological material MB, as shown in FIG. 5, using the disgregating device 10 of the invention.

As can be seen from this FIG. 5A, in the cell suspension obtained in this way the disgregated biological material, denoted by MB', conserves intact its features and functions, and in particular the cells CEL maintain their original form, just as the fragments of matrix MAT and the growth factors FC, indicative of the viability of the cells CEL, do not present alterations and modifications to the detriment of the viability and of the capacity for developing and reacting with the external conditions, represented with arrows in FIG. 5A, of the same cells CEL.

In this way each single cell CEL conserves intact all those organic and inorganic factors which involve it and constitute its biological niche and therefore determine the function and the capacities thereof, such as in particular that of developing.

Figure 6:
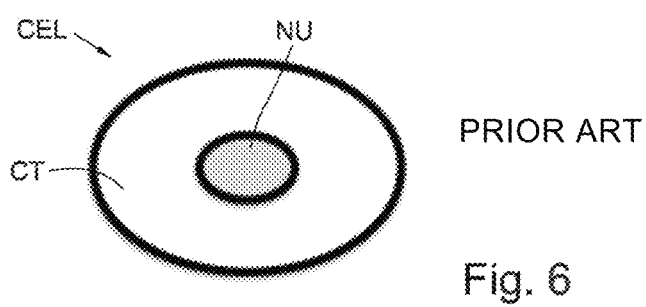
FIG. 6 illustrates schematically a single isolated cell obtained with a conventional disgregating device in accordance with the prior art.
Figure 7A:
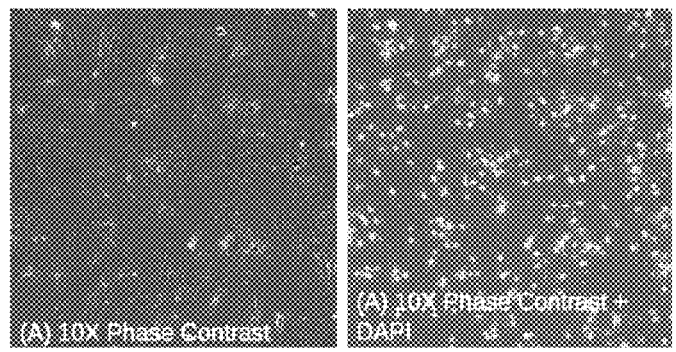
FIGS. 7A-7F are examples of slides of analysis of cell suspensions and tissue micrografts obtained using the disgregating device of biological material of the invention.
Figure 7B:
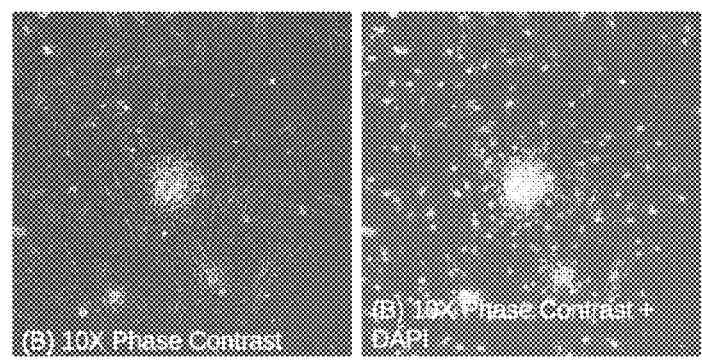
Figure 7C:
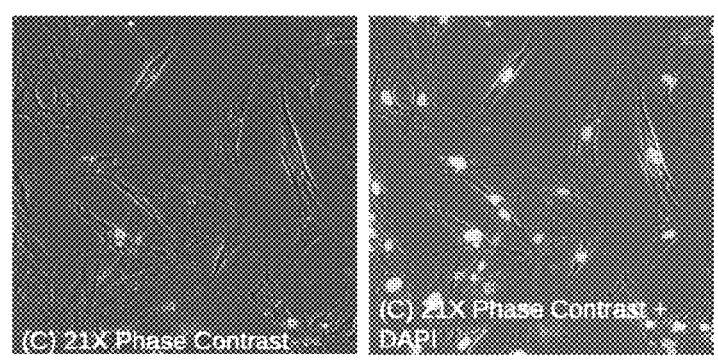
Figure 7D:
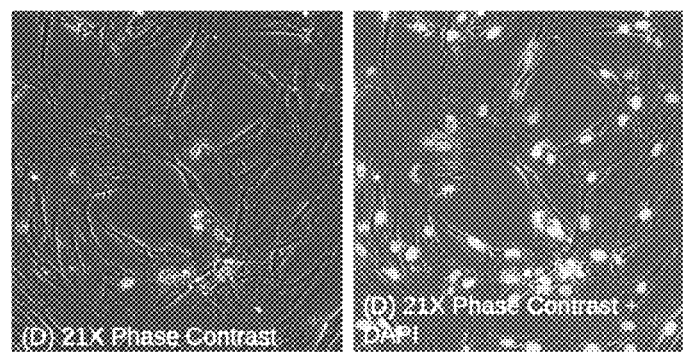
Figure 7E:
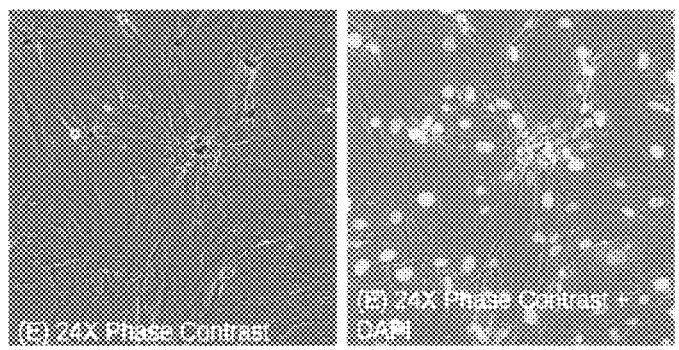
Figure 7F:
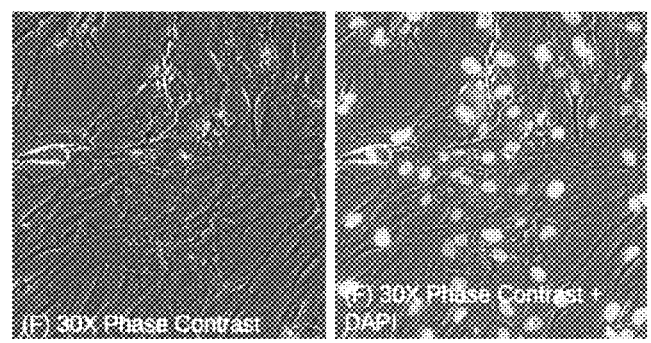

Instead, very differently, as already previously underlined and schematised in FIG. 6, in the cell suspensions which are obtained through disgregation using the techniques currently known and available, the cells have a modified form with respect to that which they had in the original biological material, not yet disgregated.

Moreover, due to the disgregation performed with conventional techniques, the cell matrix is also subject to alterations and modifications so that, in the final cell suspension obtained by disgregating the original biological material, the single cells are found to be free from all those organic and inorganic factors which involve them, in their biological niche, and determine the function and the capacities thereof.

Examples of Application of the Disgregating Device of the Invention

As anticipated the disgregating device 10 of the invention is particularly suitable and advantageous for preparing tissue micrografts and cell suspensions to be used for various purposes and in multiple applications, both typically medical and not, for example for the simple analysis in the laboratory of samples or for diagnostic or therapeutic or cosmetic purposes or others again, as ascertained by thorough and extensive tests and experiments.

Therefore, here below, referring to the block diagrams of FIGS. 4A-4D, some specific and preferred examples of use and application are to be illustrated, in various areas and for various purposes, of the disgregating device 10 of the invention and of the respective cell suspensions and tissue micrografts which are obtained, with this device, from the disgregation of biological material.

Example 1 (Ulcers, Losses of Substance, Dehiscences, Difficult Wounds)

Figure 4A:
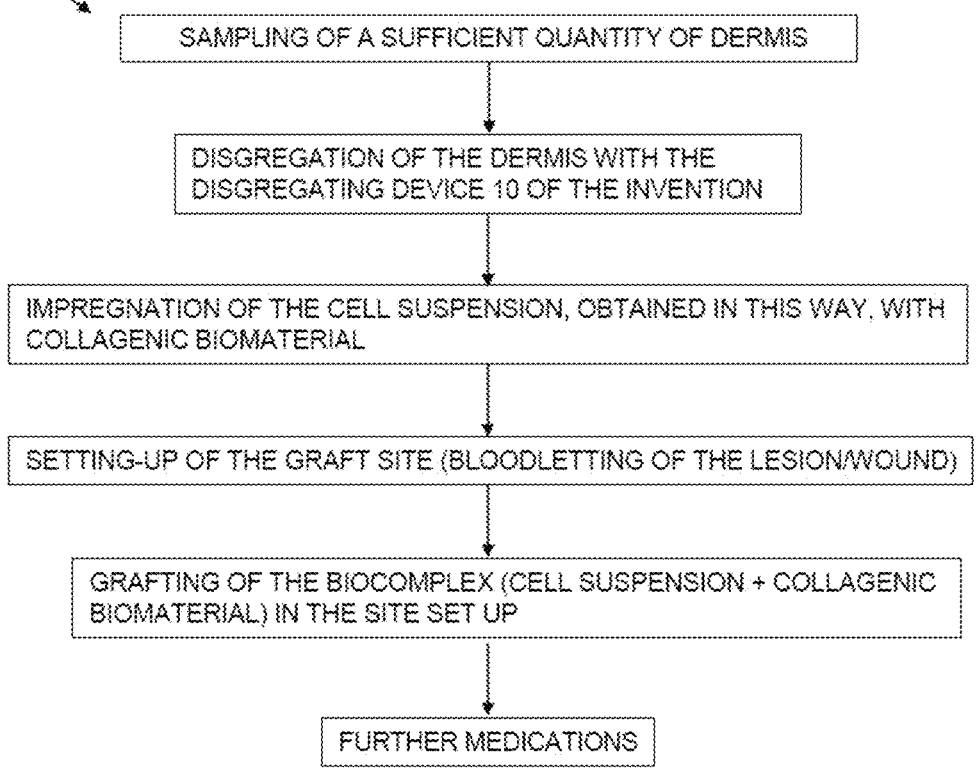
FIG. 4A-4F are block diagrams which illustrate some possible examples of application of the disgregating device of biological material of the invention and of the respective cell suspensions and tissue micrografts obtained using this disgregating device.

In this first example 1, corresponding to the block diagram of FIG. 4A, a sufficient quantity of dermis for the treatment is taken initially from an uninjured area of the human body and then its disgregation is carried out via the disgregating device 10, proposed with the invention.

Then, once the cell suspension has been obtained, it is impregnated with collagenic biomaterial.

At this point the graft site is prepared, i.e. with the bloodletting of the lesion or wound to be treated.

Then the biocomplex obtained previously is grafted in the site, made up of the cell suspension and the biomaterial, and then a common medication is performed.

Subsequently a series of periodical checks is carried out.

It is also possible to carry out further treatments in the case of very extensive lesions.

Example 2 (Aesthetic Applications)

Figure 4B:
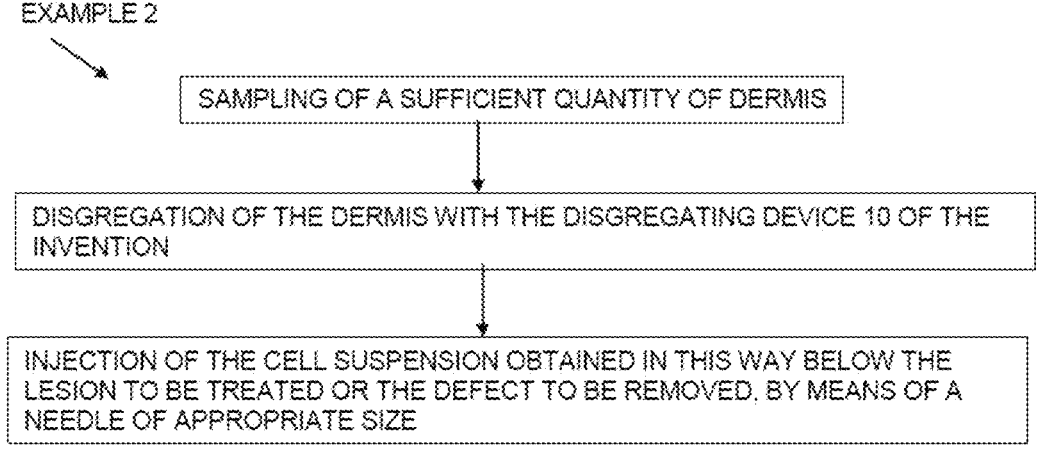

In this example 2, corresponding to the block diagram of FIG. 4B, a sufficient quantity of dermis for performing the treatment is taken initially from an uninjured area of the human body.

This quantity of dermis is then disgregated by means of the device proposed.

Once the cell suspension has been obtained it is injected under the lesion to be treated or the defect to be removed, which can be wrinkles, psoriasis, scleroderma, vitiligo, ulcer, keloid, minus, etc., with a needle of adequate size.

The usual routine checks are then carried out.

It is possible to carry out further treatments in the case of very extensive lesions.

Example 3 (Orthopaedic-Odontoiatric-Maxillofacial Applications)

Figure 4C:
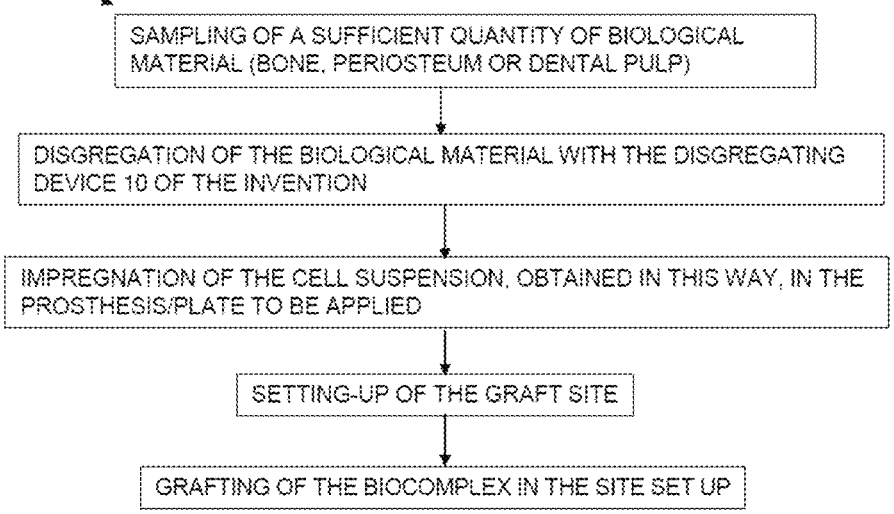

Referring to the block diagram of FIG. 4C, also according to this example 3 a sufficient quantity of biological material (bone, periosteum or dental pulp) is taken initially without drawing blood and without overheating it, and it is then fragmented and processed via the proposed disgregating device 10, so as to obtain and prepare the respective cell suspension.

Then a phase of impregnation of the biomaterial is provided, i.e. of the cell suspension, in the prosthesis/plate to be applied, so as to obtain the biocomplex.

Subsequently the receiving site is set up (bone defect of various nature, fracture, acceptor site of prostheses such as for example hip prosthesis, knee, dental implants, etc.) that is a surgical access is carried out and, after having set it up, the already prepared biocomplex is grafted in the receiving site.

Example 4 (Application in the Regeneration of Periodontal Defects)

Figure 4D:
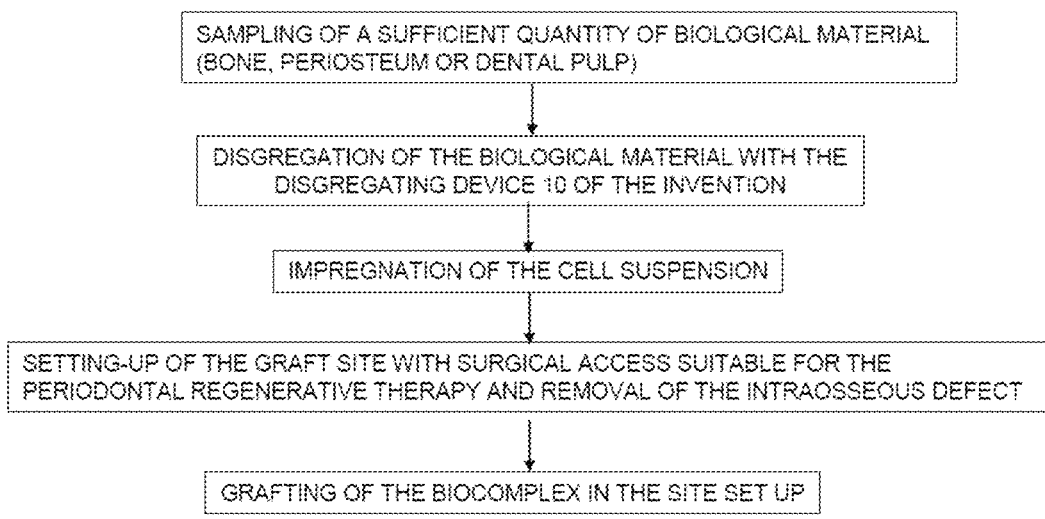

In this example 4, corresponding to the block diagram of FIG. 4D, after having taken initially a sufficient quantity of biological material (bone, periosteum or dental pulp) without drawing blood and without overheating it, it is fragmented and processed via the proposed disgregating device 10.

Impregnation is then carried out of the biomaterial obtained for disgregation, thus preparing the biocomplex.

The receiving site is then set up.

In particular in this phase a surgical access is made in the zone of the site with incision flaps suitable for the periodontal regenerative therapy and a debridement is also carried out, i.e. removal of the intraosseous defect with conventional techniques.

Subsequently, after having set up the receiving site, the biocomplex obtained is grafted.

Finally suture of the site is performed in a contenitive manner and the patient is referred for successive checks.

Example 5 (Veterinary Applications)

Figure 4E:
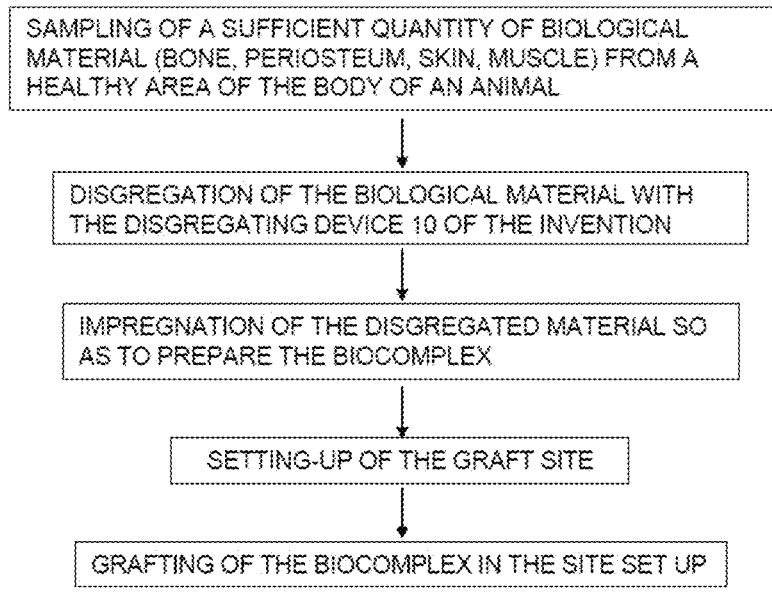

In this example of application 5, in the veterinary field, corresponding to the block diagram of FIG. 4E, the biological material, after having been initially taken in a sufficient quantity from a healthy zone of the body of an animal (bone, periosteum, skin, muscle) without drawing blood and without overheating it, is fragmented and processed by means of the disgregating device 10, proposed.

Impregnation is then carried out of the biomaterial obtained for disgregation, thus preparing the biocomplex.

The receiving site is then set up.

In particular in this phase a surgical access is made in the zone of the site with incision flaps suitable for regenerative therapy and a debridement is also carried out with conventional techniques.

Subsequently, after having set up the receiving site, the biocomplex previously prepared is grafted.

Finally suture of the site is performed in a contenitive manner and the animal is referred for successive checks.

Example 6 (Application in the Regeneration of Muscular and Myocardial Defects)

Figure 4F:
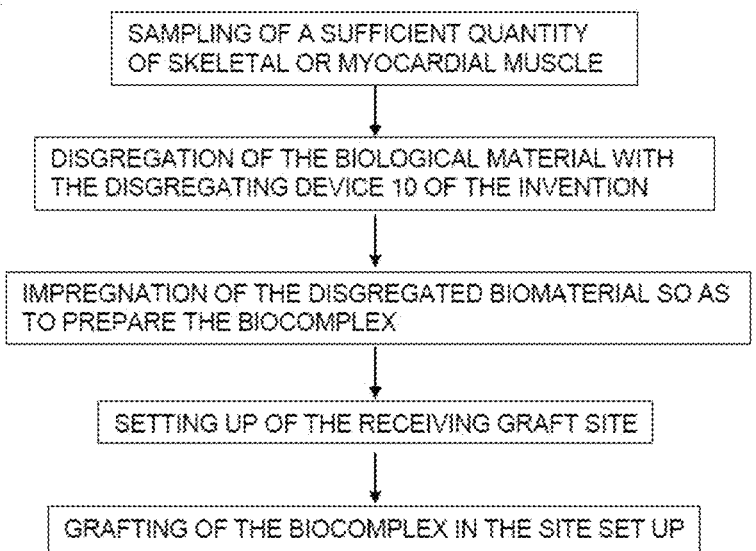

In this example 6, corresponding to the block diagram of FIG. 4F, a sufficient quantity of skeletal or myocardial muscle is initially taken without drawing blood and with mini-invasive access, and it is then fragmented and processed by means of the proposed disgregating device 10.

Impregnation is then carried out of the biomaterial obtained for disgregation, so as to prepare the biocomplex.

The receiving site is then set up.

More particularly in this phase a surgical intervention is performed in the zone of the site with a mini-invasive access and the biocomplex which had been prepared is then grafted.

The patient is then referred for subsequent checks.

Experiment Results and Tests

The disgregating device 10 and the relative products, i.e. the cell suspensions and the samples obtained with this device for disgregation of an original biological material, were the subject of numerous and in-depth experimental checks and tests aimed at collecting useful data and at confirming the innovative features and the advantages of the present invention.

For completeness, the images of FIGS. 7A-7F show some examples of slides and samples which have been analysed and examined as part of these tests and therefore can be clearly understood and interpreted by skilled persons, wherein these samples, the subject of analysis and study, were obtained from a disgregated tissue by means of the disgregating device 10 of the invention of biological material.

In detail the laboratory analyses performed on these samples have shown that the first colonies appeared after approximately 15-20 days and a month after sowing.

These two colonies were then detached from the dish and resown, photographed and analysed cytofluorimetrically.

Now, as can be seen from the images of FIGS. 7A-7F, the samples analysed, derived from the disgregated original tissue, clearly have two different populations of cells, i.e. a first population with an elongated shape and a second population with a rhomboid shape, larger.

In this respect it is pointed out that in order to be able to photograph these two populations of cells the respective nuclei were coloured blue with a fluorescent organic dye (DAPI), while for the cytofluorimetric analysis the panel of antibodies was used which is normally used for characterising mesenchymal cells, plus an anti-CD11b antibody.

To sum up, these analyses gave the following results:
viability: 92%
CD90+ cells: 52%
CD105+ cells: 82%
CD11b+ cells: 45%
CD11b-dim cells: 43%
CD73+ cells: 82%
CD146+ cells: 36%
CD146-dim cells: 49%
CD31+ cells: 2%
CD80+ cells: 3%
CD45+, CD14+, CD34, CD133 cells: 0%

Moreover it resulted from these tests that the cells are found to belong to the mesenchymal lineage and, as was expected, are negative to the markers of the hematopoietic lineage.

Moreover the viability of the cells was found to be excellent.

Figure 8:
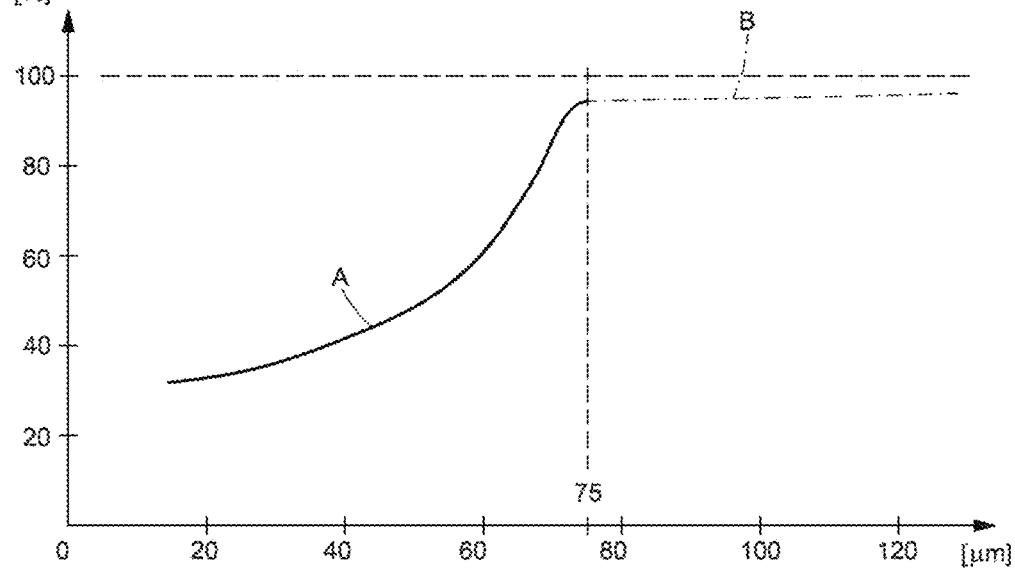
FIG. 8 is a qualitative diagram which shows the percentage of the viable cells in a cell suspension, obtained with the disgregating device of the invention, as a function of the dimensions of the microholes of a disgregating grid included in the same device.

More particularly the qualitative diagram of FIG. 8, which summarises and condenses the numerous tests performed to ascertain the features and the advantages of the present invention, clearly shows that, in the cell suspension obtained by means of the disgregating device 10 of the invention, the percentage of viable isolated cells and of the respective growth factors reaches its maximum and optimal value when the holes 13a of the disgregating grid 13 have size or a diameter of around 75 microns.

Instead, for values of the size of the holes 13a below 75 microns, this percentage of the viable isolated cells is substantially lower than the maximum value, as shown by the portion A with continuous line of the diagram of FIG. 8.

The portion B, with dotted and dashed line, of the diagram of FIG. 8 in turn should be referred to the presence, in the cell suspension obtained by means of the disgregating device 10 of the invention, as well as of isolated cells also of agglomerates of cells.

Therefore these tests, as moreover others not given here for reasons of brevity, have clearly demonstrated that the disgregating device 10, proposed by the present invention, allows the preparing and obtaining of samples of biological tissue and more generally of biological material, obtained through disgregation of a tissue that is of an original biological material, wherein advantageously the samples obtained and in particular the respective cells conserve intact and unaltered the features, the functions and the cell viability of the tissue and of the original biological material and therefore are not altered by the phase of disgregation whereto they have been subjected, with the further advantage that the samples obtained, being intact and conserving their original cell viability, are suitable to be analysed directly without resorting to the aid of chemical reagents.

In this respect it will certainly be appreciated that the disgregating device 10 of the present invention constitutes a significant improvement and an important innovation with respect to the prior art, in particular constituted by the shredding device described in the U.S. Pat. No. 5,731,199, both in the method of manufacture of the parts which are essential for the working of the disgregating device and as regards its use and its potential applications, and in particular allows a considerable expansion of the field of application of the disgregating device with respect to that allowed by the device known from the U.S. Pat. No. 5,731,199.

Variants and Improvements

Without prejudice to the basic concepts of the present invention it is also clear that changes and further improvements may be made to the disgregating device of biological material, described hitherto, for the preparation of cell suspensions and tissue micrografts, without thereby departing from the scope of the same invention.

For example the blades of the bladed rotor 14 can be more than one, i.e. can be four or six placed symmetrically around the tip area of the shaft 14*a*.

Figure 3C:
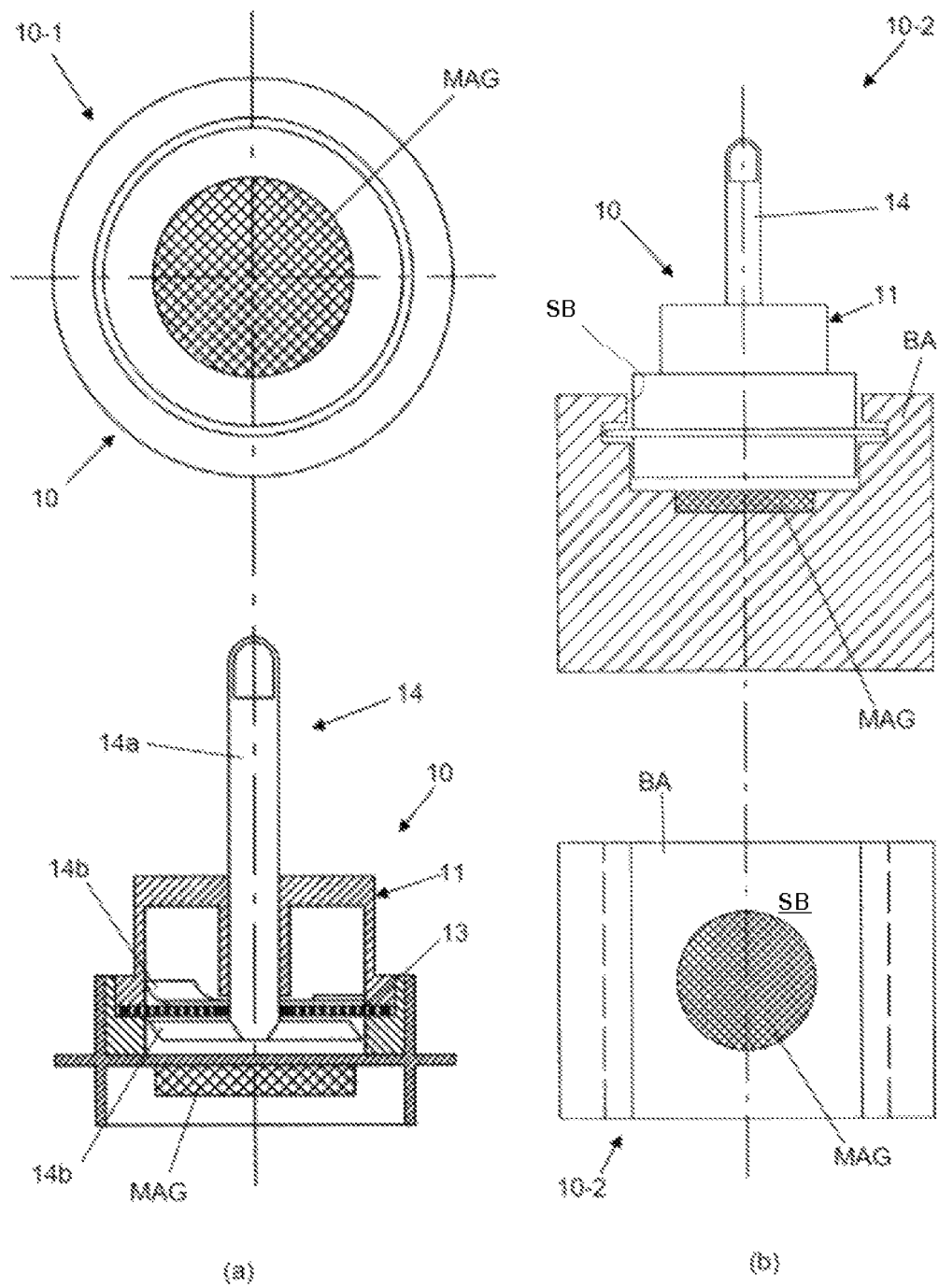
FIG. 3C, divided into sections (a) and (b), shows in a plan view and sectioned some improving variants of the disgregating device of the invention comprising a magnetic element having the function of controlling the pressure applied by the bladed rotor on the disgregating grid in order to disgregate the biological material.

Again, according to an improvement corresponding to the embodiments shown in FIG. 3C, the disgregating device 10 of the invention can be associated with a magnetic element having the function of appropriately controlling the pressure with which the bladed rotor 14 and the disgregating grid 13 co-operate one with the other in order to disgregate the biological material.

In detail, in a first embodiment denoted by 10-1 and shown in section (a) of FIG. 3C, the disgregating device 10 is provided with a magnetic element, denoted by MAG and constituted in particular by a permanent neodymium magnet, which is glued to the base of the tray or lower collecting chamber 12*b* of the disgregating device 10.

Instead, in a second embodiment denoted by 10-2 and shown in section (b) of FIG. 3C, the disgregating device 10 is provided in combination with an additional support base BA and the magnetic element MAG is attached on the base of a seat SB which is formed in this additional support base BA and has the function of receiving and housing stably during use the disgregating device 10.

This magnet MAG performs the action, in both embodiments 10-1 and 10-2, of attracting the helical blade 14*b* of the bladed rotor 14 with a pre-established load, so as to control the pressure applied by the same bladed rotor 14*b* on the disgregating grid 13 and in particular avoid an excessive value of this pressure.

For this purpose, the two parts which in the disgregating device 19 co-operate in contact and in ratio of pressure one with the other to disgregate the biological material, i.e. the helical blade 14*b* of the bladed rotor 14 and the disgregating grid 13, are made of up of steels exhibiting different allotropic phases, austenitic or martensitic, so that the disgregating grid 13, made for example with 316L stainless steel therefore austenitic steel, is amagnetic and therefore insensitive to the magnetic field generated by the magnet MAG, whereas instead the helical blade 14*b*, made with martensitic steel, is sensitive to the magnetic field generated by the magnet MAG and is therefore pushed with a controlled pressure or force against the disgregating grid 13.

Obviously the permanent magnet MAG is dimensioned and selected in terms of power and capacity of attraction in such a way that the pressure applied by the helical blade 14*b* against the disgregating grid 13 is adequate for obtaining a correct disgregation of the biological material.

Therefore, to sum up, these variants 10-1 and 10-2 of the disgregating device of the invention have the advantage of keeping effectively under control the pressure applied by the helical blade or rotor 14*b* against the disgregating grid 13, so as to obtain an optimal disgregation of the biological material and therefore prevent and remedy some disadvantages which can occur in known disgregating devices, such as for example that described by the U.S. Pat. No. 5,731,199, in which this control is lacking.

Use of the Disgregating Device of Biological Material of the Invention in the Operating Theatre, with the Disgregating Device Connected by Means of an Adapter to a Surgical Wand Included in the Instrument Supply of the Operating Theatre Finally, according to a further aspect of the present invention, the disgregating device 10 of biological material, illustrated previously, can be advantageously connected, with the aid of an appropriate adapter, to a usual surgical wand or electric motor, sterile, already present in the operating theatre, so as to allow use of the disgregating device 10 of the invention directly in the operating theatre.

Figure 3D:
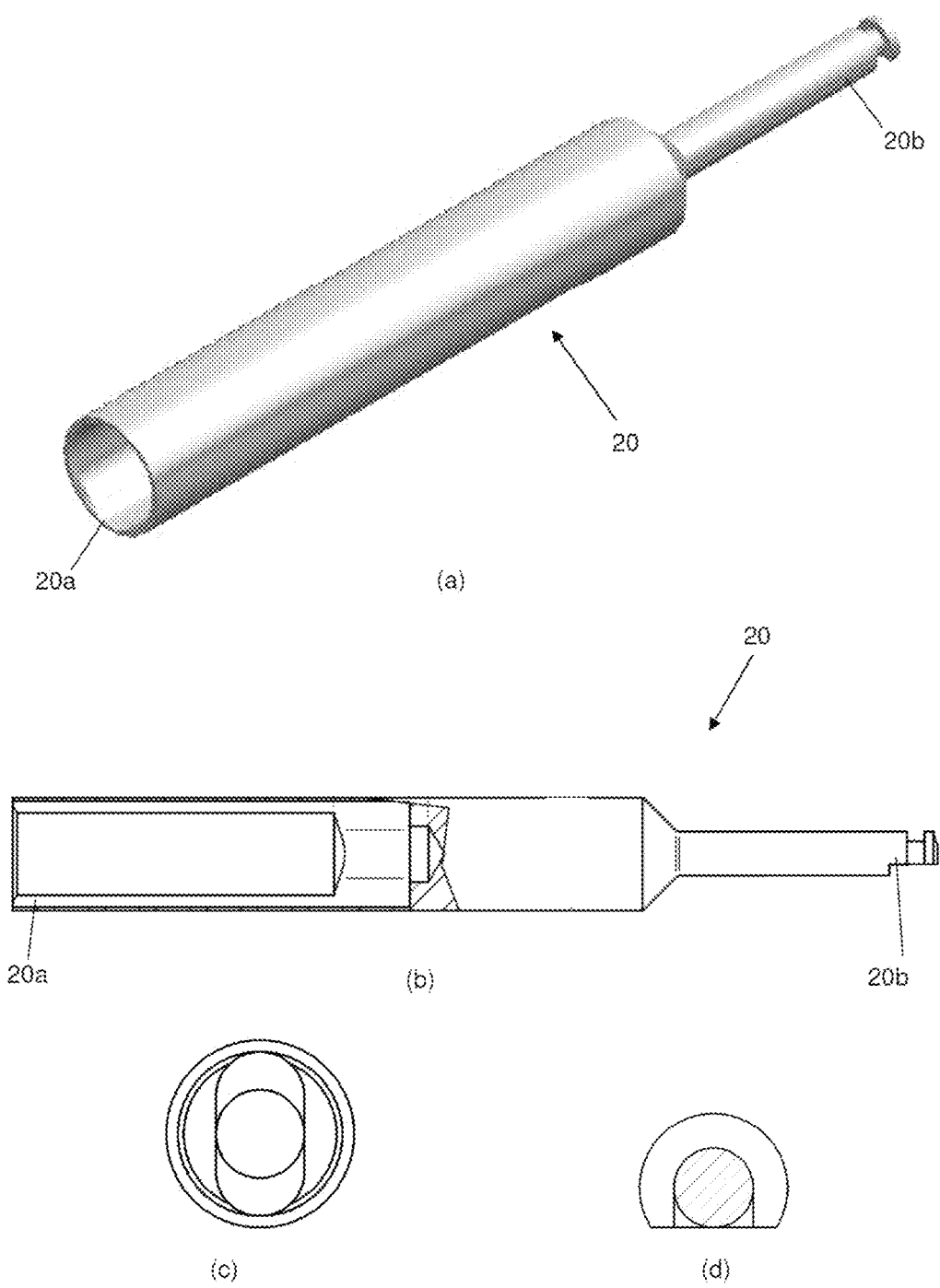
FIG. 3D, divided into sections (a), (b), (c), (d), shows in three-dimensional graphic form, in a longitudinal view, and sectioned in the end zones, an adapter apt to be coupled with the disgregating device of the invention in order to connect it to a surgical wand in the usual instrumental supply of an operating theatre.

FIG. 3D shows this adapter, denoted in general by 20, which allows in fact the connection of the disgregating device 10 of the invention to a common surgical motor or manipulator, included in the supply of sterile devices and instruments usually present in the operating theatre.

In detail the adapter 20 has an elongated configuration with a first end 20*a* apt to connect the adapter 20, on one side, to the shaft 14*a*, projecting, of the disgregating device 10, and a second opposite end 20*b*, appropriately shaped, apt to connect the adapter 20, on the other side, to the surgical wand, already present in the operating theatre.

In effective use this adapter 20 is connected, in the operating theatre, on the one side to the projecting shaft 14*a* of the disgregating device 10 and on another side to the surgical wand.

The surgical wand is then actuated so as to rotate at an appropriate speed, in particular 80 rpm, and applying an appropriate torque, for example of 25/Nw*cm, as already indicated previously, the bladed rotor 14 of the disgregating device 10 and consequently cause the disgregation of the biological material, already taken from the patient being treated in the operating theatre and previously introduced into the disgregating device 10.

In this way, i.e. without transferring to the exterior of the operating theatre the biological material taken from the patient, it is possible to prepare the disgregated biological material, for example in the form of a tissue micrograft, to be reinserted in the body of the patient who is being treated in the operating theatre.

Therefore the disgregating device 10 of the invention, thanks to the adapter 20 described previously, allows innovative performances and results which go far beyond those permitted by the prior art, for example by the shredder device of biological material described by the U.S. Pat. No.

5,731,199 already cited several times previously, so as to constitute a valid alternative to the known systems currently in use.

In particular the disgregating device 10 of the invention, used in combination with this adapter 20 which allows the connection thereof with a sterile surgical wand, already present in the operating theatre, is no longer configured as a simple disgregating device of biological material, such as that described by the U.S. Pat. No. 5,731,199, but becomes and can be compared, at least functionally, with a surgical instrument which can be directly used in the operating theatre, i.e. to a sterile and single-use microscalpel, constituted by a plurality of microblades, for example 600, supposing that the disgregating grid 13 of the device 10 has 100 microholes or hexagonal pores, i.e. 100 microholes each one defining 6 microblades, therefore a total in fact of 600 microblades, wherein this microscalpel can be used to cut and disgregate the tissues in a few minutes in order to obtain, directly in the operating theatre and without further processes, the tissue fragments of calibrated dimensions which are required for the patients being treated in the operating theatre.

Consequently, at least within the sphere of this innovative use, the disgregating device 10 of the invention could be also defined as a microscalpel for mini-invasive microsurgery.

In this respect it is underlined that to date the prior art did not allow these performances and results in the operating theatre, which are obtained instead from the disgregating device 10 connecting it, as mentioned, via the adapter 20 to a common surgical wand already present in the operating theatre.

In fact, in the prior art, therefore also including the shredder device described by the U.S. Pat. No. 5,731,199, it was necessary, in order to obtain the microfragments of tissue to be used in the operating theatre for treating the patient, to transfer the tissues, once taken from the patient, outside of the operating theatre, into a laboratory equipped with a special machine having the function of activating or rotating the device, so as to obtain the microfragments of tissue, to be taken then into the operating theatre to be grafted in the patient.

This transfer outside of the operating theatre and the operations associated therewith entailed however manipulations which by law were not permitted in the sphere a medical therapy.

Instead, as described previously, by connecting via the adapter 20 the disgregating device 10 of the invention with a surgical manipulator included in the supply of instruments and devices, sterile, already present in the operating theatre, it is possible to make available and to use the device 10 directly in the operating theatre, conserving the sterility and the efficiency of the system and at the same time observing the law.

Therefore, in this way, the disgregating device of the invention becomes also an essential part of an innovative instrumental clinical and surgical procedure, for the regeneration of tissues in the operating theatre, apt to observe the conditions of sterility, procedure which was not instead possible to perform before with the instruments offered by the prior art, in particular with the device described by the U.S. Pat. No. 5,731,199.

Moreover in addition to the aforementioned advantages and performances, already in itself important, related to the use of the device 10 of the invention directly in the operating theatre, it is to be considered that the same device 10 is characterised, as illustrated extensively previously, by an innovative technology and process for the formation of microholes 13a of the respective disgregating grid 10.

Consequently, as already underlined previously, the disgregating device 10 is configured in fact and can be rightfully compared to a surgical mill or miniscalpel provided with a plurality of microblades, for example in a number of 600, in order to cut and fragment the tissue of the patient to be treated in the operating theatre.

The invention claimed is:

1. A disgregating device of biological material for the preparation of cell suspensions or tissue micrografts or microfragments of tissue, comprising:
    a hollow outer body, defining an inner chamber;
    a perforated plate or disgregating grid, fixed, having a plurality of microholes provided with sharp edges, said disgregating grid being housed transversely in said inner chamber so as to define an upper loading chamber apt to be loaded with the biological material to be disgregated and a lower collecting chamber apt to collect the biological material, once disgregated; and
    a bladed rotor, rotating in said inner chamber, said bladed rotor being apt to co-operate, rotating, with said disgregating grid, fixed, so as to feed and bring the biological material, contained in the upper loading chamber, into contact and to co-operate with the microholes, with sharp edges, of said disgregating grid, and therefore cause the disgregation of the biological material while it passes through said microholes;
    wherein the microholes of said perforated disgregating grid have dimensions or a diameter between 70 μm and 80 μm,
    wherein the microholes of said disgregating grid are formed by means of a die-punch process, using a moulding punch which is a polygonal-based pyramid-shaped punch,
    wherein said moulding punch and a corresponding die are configured in such a way that each of said microholes is obtained through breakage and tearing of the material of a metal sheet and has an irregular sharp edge defining a plurality of sharp tips, and
    wherein said outer body defines a through hole, substantially vertical and distinct from the inner chamber, the through hole extends in an external wall of the outer body between an upper edge of said outer body and a base of said collecting chamber, wherein said through hole has the function of allowing the extraction of the disgregated biological material, accumulated in said collecting chamber,
    whereby said disgregating device is apt to prepare cell suspensions and set up tissue micrografts that preserve intact the characteristics and cell viability of the original biological material, not disgregated, thereby avoiding the use of chemical reagents in the preparation of these cell suspensions and in the setting-up of said tissue micrografts.

2. The disgregating device of biological material according to claim 1, wherein said outer body is associated with a secondary internal body, defining said upper loading chamber, and is constituted by an upper portion defining a seat which houses said secondary internal body and a lower portion that defines said lower collecting chamber,
    wherein said disgregating grid is interposed between said secondary internal body and the lower portion of said outer body, and
    wherein said secondary internal body forms a support seat for rotatably supporting said bladed rotor and said secondary internal body is coupled to the upper portion of said outer body so as to be fixed relative to said outer body and to fix the disgregating grid relative to said outer body.

3. The disgregating device of biological material according to claim 1, wherein each microhole of said disgregating grid is surmounted by a plurality of blades.

4. The disgregating device of biological material according to claim 1, further comprising a cover, removable, for covering said upper loading chamber, wherein said bladed rotor extends through a hole formed in said cover, whereby said bladed rotor partially protrudes at a respective upper end from said cover so as to allow the coupling of said bladed rotor with suitable motor means apt to control a rotation of said bladed rotor in said inner chamber.

5. The disgregating device of biological material according to claim 1, wherein said bladed rotor comprises:

a shaft, arranged in the vertical direction;

a distributing blade, associated with a lower end of said vertical shaft and exhibiting a curved helical shape; and a lower scraper, also associated with the lower end of said vertical shaft, wherein the disgregating grid, fixed, is interposed between said helical distributing blade and said lower scraper, said helical distributing blade and said lower scraper associated with the lower end of said vertical shaft, whereby said helical distributing blade of the bladed rotor is configured to co-operate with an upper face of said disgregating grid facing towards said upper loading chamber, in order to distribute and bring the biological material to be disgregated into contact with the microholes of the disgregating grid, and said lower scraper of the bladed rotor is configured to co-operate with a lower face of said disgregating grid facing towards said collecting chamber, in order to scrape the disgregated biological material from said disgregating grid and discharge the disgregated biological material in said collecting chamber.

6. The disgregating device of biological material according to claim 5, wherein said scraper is formed by a plurality of blades which extend radially from the lower end of the shaft of said bladed rotor.

7. The disgregating device of biological material according to claim 1, wherein the disgregating device comprises a magnetic element that attracts the helical blade of the bladed rotor and controls a pressure applied by the bladed rotor on the disgregating grid.

8. The disgregating device of biological material according to claim 7, wherein the magnetic element is attached to the base of the lower collecting chamber of the disgregating device.

9. The disgregating device of biological material according to claim 7, wherein the magnetic element is attached on the base of a seat formed in an additional support base, wherein the seat has the function of receiving and housing the disgregating device during use.

* * * * *